United States Patent [19]

Ray

[11] 4,328,813
[45] May 11, 1982

[54] BRAIN LEAD ANCHORING SYSTEM

[75] Inventor: Charles D. Ray, Wayzata, Minn.

[73] Assignee: Medtronic, Inc., Minneapolis, Minn.

[21] Appl. No.: 199,014

[22] Filed: Oct. 20, 1980

[51] Int. Cl.³ ............................................. A61N 1/04
[52] U.S. Cl. .................................................. 128/791
[58] Field of Search ............... 128/639, 642, 783, 784, 128/785, 791, 303 B, 748

[56] References Cited

U.S. PATENT DOCUMENTS

| | | | |
|---|---|---|---|
| 3,055,370 | 9/1962 | McKinney et al. | 128/303 B |
| 3,115,140 | 12/1963 | Volkman | 128/303 B |
| 3,187,745 | 6/1965 | Baum et al. | 128/639 |
| 3,469,577 | 9/1969 | Kater | 128/639 |
| 3,964,470 | 6/1976 | Trombley | 128/642 |

FOREIGN PATENT DOCUMENTS 578954  11/1977  U.S.S.R. .............. 128/639

Primary Examiner—William E. Kamm

Attorney, Agent, or Firm—Schroeder, Siegfried, Vidas, Steffey & Arrett

[57] ABSTRACT

A system for anchoring a brain lead within a cranial burr hole while closing that hole. A socket is provided with an aperture defining a lead passage and is engageable with the cranial burr hole to secure the socket to the cranium with the lead passage aperture in general alignment with the burr hole. A plug is configured to cooperate with the socket lead passage aperture for mutual engagement of a lead within the aperture while closing that aperture. In a preferred embodiment, the socket includes a split grommet portion formed of a flexible material that is biased to maintain the grommet split open. The socket aperture has a neck portion of reduced size with the plug being configured to engage that neck portion and resist removal of the plug from the socket aperture. The socket is also provided with a flange surrounding the grommet portion with holes in the flange being engageable by a tool to facilitate closure of the grommet split for insertion of the socket in a cranial burr hole.

17 Claims, 4 Drawing Figures

BRAIN LEAD ANCHORING SYSTEM

DESCRIPTION

1. Background of Prior Art

Electrical stimulation of the brain is under increasing use and review for such varied purposes as relief of chronic pain and treatment of movement disorders. Typically, a cranial drill (commonly referred to as a burr) is employed to provide access to the brain at a suitable skull location. Thereafter, following preparation and stimulation site determination, the stimulation lead is placed with electrode(s) positioned at the desired stimulation site(s). After satisfactory testing of the results of stimulation, it is often critical that the electrode not be moved. One millimeter of lead travel may be critical. Thus, reliable anchoring of the lead is necessary.

After the lead implant procedure, and following the removal of all implements other than the stimulation lead, it is necessary to close the cranial burr hole. In the prior art, this has been accomplished with plugs of various designs or with a cranioplasty/acrylic material. In the former case, plug designs known to the inventor of the present invention that accomplish the dual purposes of closing the cranial burr hole while maintaining the desired lead and electrode position are cumbersome. In the latter case, the reliability of the lead anchoring is uncertain, at least initially.

2. Brief Summary of the Invention

The present invention provides a simple and reliable system for anchoring a lead within a cranial burr hole while closing that hole. A socket is provided which includes an aperture defining a lead passage and which engages the cranial burr hole to secure the socket to the cranium with the lead passage aperture in general alignment with the burr hole. A plug is configured to cooperate with the socket aperture for mutual engagement of a lead within the passage while closing the aperture. In a preferred embodiment, the socket is formed of a flexible material having a split grommet portion and a flange, the flange containing holes which may be engaged by a tool to facilitate a temporary closing of the split grommet during insertion of the grommet portion into the burr hole. The inner walls of the grommet portion define the lead passage aperture with that aperture having a neck portion of reduced size. The plug is configured to engage the neck portion and resist removal of the plug and a closing of the grommet split. The outer walls of the grommet portion may be provided with ribs to engage the walls of the cranial burr hole for greater security in the engagement between the socket and the cranium. The grommet split allows positioning of a lead within the lead passage without requiring access to a lead end. This is especially useful when the lead is already in place, as a result of an emergency procedure, for example. The anchoring system of the present invention may be employed with a stimulation lead, a sensing lead, a combination thereof or any other elongated member requiring passage through the cranium.

DETAILED DESCRIPTION OF THE INVENTION

The present invention allows communication with the brain through a cranial burr hole while closing that hole and anchoring the communication device. Typically, the communication device will be an electrical stimulation lead. However, for the purposes of this specification and claims, the term "lead" is intended to embrace a stimulation lead, a sensing lead, a combination thereof or any other elongated member, such as a catheter, which may usefully be passed through a cranial burr hole.

Figure 1:
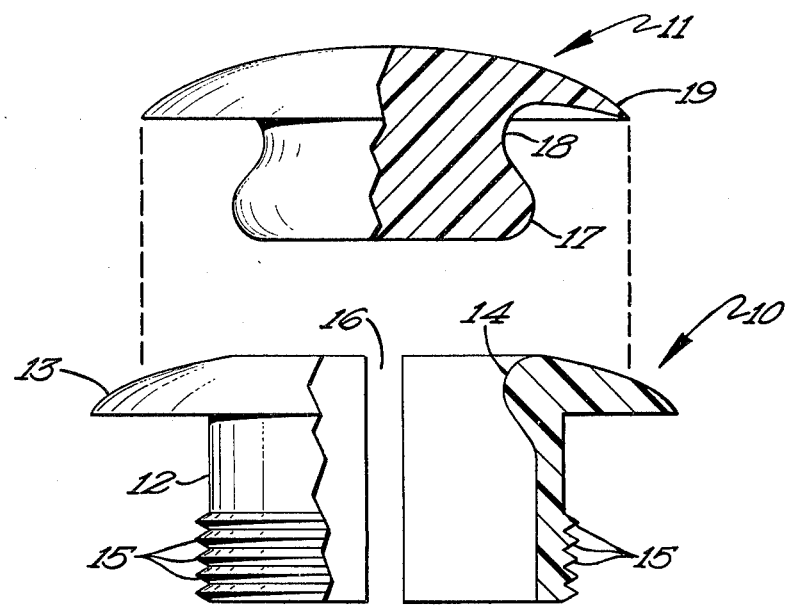
FIG. 1 is an exploded view illustrating, in cross section, the two components that form a preferred embodiment of the present invention.

FIG. 1 illustrates an exploded view of a preferred embodiment of the present invention, in cross section, including a socket member 10 and a plug member 11. The socket member 10 includes a grommet portion 12 and a flange portion 13, the inner walls of the grommet portion 12 defining an aperture for passage of a lead through the cranium. The aperture includes a neck portion 14 of reduced diameter whose purpose will be explained more fully below. The periphery of the outer wall of the grommet portion 12 may be provided with circumferential ribs as indicated at 15, the ribs 15 engaging the side wall of a burr hole to enhance the security of the engagement of the grommet outer wall with the burr hole side wall. The socket 10 is split as indicated in the grommet portion 12 in FIG. 1 at 16 with the split being biased open to allow an insertion of the grommet portion 12 within the burr hole in the manner to be described more fully below.

The plug 11 is configured to cooperate with the aperture defined by the inner walls of the grommet portion 12, including a portion 17 generally coextensive with the aperture defined by the inner walls of the grommet portion 12 and a reduced diameter portion 18. A flange portion 19 is configured to overlie the socket flange portion 13. The reduced diameter portion 18 of plug 11 has a reverse configuration to the neck 14 of socket 10 such that the surfaces of the plug portion 18 and neck 14 will mate on insertion of the plug 11 within the socket 10 with the portion 17 underlying the neck portion 14 and the flange 19 overlying the flange 13. The plug 11 is formed of a resilient material to facilitate its insertion into the aperture in the socket 10, and particularly the passage of the portion 17 past the neck 14, while the socket 10 is formed of a flexible material biased to maintain the split 16 open but allowing a closure of the split 16 for insertion of the grommet portion 12 within a cranial burr hole. With the socket 10 in position within a cranial burr hole, the open split bias of the socket 10 will cause the outer walls of grommet portion 12, and particularly ribs 15, to engage the burr hole side walls and secure the socket 10 to the cranium. Placement of the plug 11 within the socket 10 will restrict a closure of the split 16 to further enhance the security of the socket 10 within the burr hole.

Figure 2:
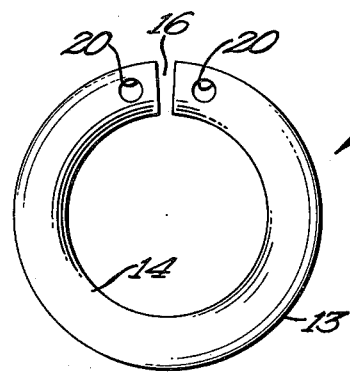
FIG. 2 is a top view of one of the components of FIG. 1.

FIG. 2 illustrates a top view of the socket 10 including a flange 13 and split 16. Positioned on either side of the split 16 in the flange 13 are holes or recesses 20 which may be engaged by a tool to temporarily close the split 16 thereby reducing the diameter of the grommet portion 12 and and allowing its insertion within a cranial burr hole. On release of the tool, the split 16 will reopen due to the flexibility of the material from which the socket 10 is formed and its bias to maintain the split 16 open. The resting diameter of the grommet portion 12 of the socket 10 is normally greater than the cranial burr hole, which is of known diameter. Thus, on closure of the split 16, and positioning of the grommet portion 12 of socket 10 within the cranial burr hole and release of the elements 20, the grommet 12 will tend to expand to a diameter larger than the burr hole within which it is contained. In this condition, the outer wall of the grommet portion 12 will engage the side wall of the burr hole and tend to maintain the socket 10 within the burr hole. As noted above, the circumferential ribs 15 enhance the reliability of this engagement. In position, the under portion of flange 13 is intended to rest atop the cranium surrounding the cranial burr hole and acts to prevent a complete passage of the socket 10 through the burr hole.

Figure 3:
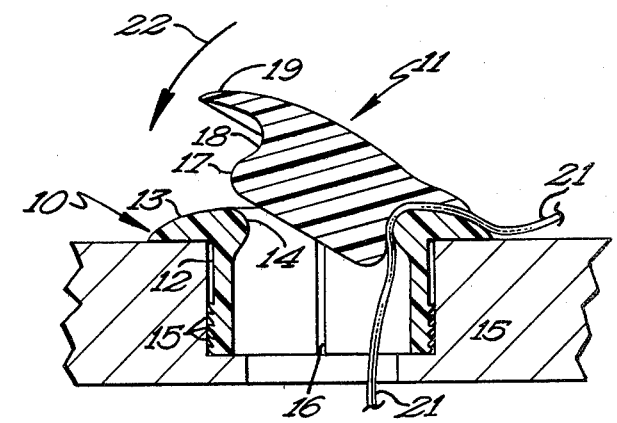
FIG. 3 illustrates the cooperation between the components illustrated in FIG. 1.

FIG. 3 illustrates a socket 10 in position within a cranial burr hole which typically has a stepped diameter for reasons well known to those familiar in the art. The length of the grommet portion 12 of the socket 10 should be no longer than the distance from the cranial surface to the step such that the flange 13 can rest atop the cranium. A lead 21 may be positioned through the cranial burr hold prior to placement of the anchoring system of the present invention. This is facilitated by the split 16 which allows passage of the lead 21 through that split and into the lead passage aperture formed by the inner walls of the grommet portion 12 without requiring access to a lead end. With the lead positioned in the desired location, and in the lead passage of the socket 10, the flange 13 is engaged by a tool at the elements 20 and the split closed while the grommet portion 12 is placed within the burr hole. On release of the flange 13 by the tool, the grommet 12 will expand within the burr hole to engage its side walls and secure the socket to the cranium. The lead 21 may be then draped over the neck 14 and flange 13 to be engaged at the neck 14 by the portion 18 of plug 11. This is illustrated in FIG. 3. An additional force applied to the plug 11 in the direction of the arrow 22 will cause the plug 11 to further enter the aperture in the socket 10 and, due to the resilience of the plug 11 material, the portion 17 will pass the neck portion 14 of the socket 10. During this process, cooperation between the portion 18 of plug 11 and the neck 14 of socket 10 will maintain the lead 21 in its desired position.

Figure 4:
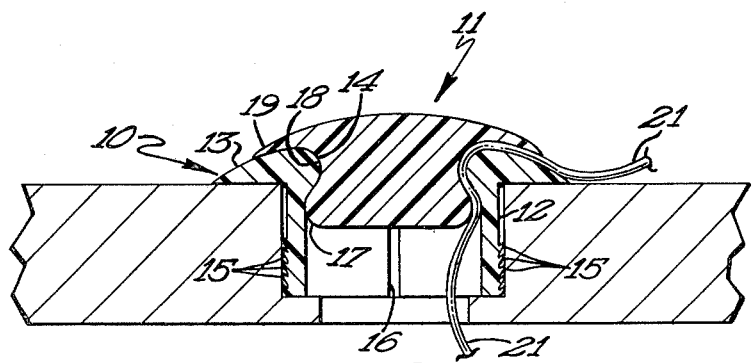
FIG. 4 further illustrates the cooperation between the components illustrated in FIG. 1.

FIG. 4 illustrates the anchoring system of the present invention with the plug inserted within the aperture of the socket 10 and at least the neck 14 and portion 18 of plug 11 mutually engaging the lead 21 to maintain it in position while the plug 11 closes the aperture in the grommet 12 and the cranial burr hole. The plug also acts against a closing of the socket split 16. After the lead 21 is anchored as illustrated in FIG. 4, the low profile of the anchoring system allows the scalp to be positioned over the socket 10 and plug 11 with a minimum of cosmetic disfigurement. The lead 21 may be tunneled under the scalp to a remote location for attachment to a source of electrical stimulation, a sensing system or to a source of material that is desired to transmit from outside the body to the brain. Also, beyond the flexibility of the socket portion 10 and the resilience of the plug material 11, any suitable materials may be employed within the system of the present invention.

Obviously, many modifications and variations of the present invention are possible in light of the above teachings. It is therefore to be understood that, within the scope of the appended claims, the invention may be practiced otherwise than as specifically described.

I claim:

1. A system for anchoring a brain lead within a cranial burr hole while closing that hole which comprises:
    socket means including an aperture defining a lead passage and means for engaging a cranial burr hole to secure said socket means to the cranium with said passage in general alignment with said burr hole; and
    plug means configured to cooperate with said socket means aperture for mutual engagement of a lead within said aperture while closing said aperture.

2. The lead anchoring system of claim 1 wherein said socket means comprises split grommet means, said aperture being formed by the inner wall of said grommet means, and said burr hole engaging means comprising the outer wall of said grommet means.

3. The lead anchoring system of claim 2 wherein said socket means is biased to open said grommet means split.

4. The lead anchoring system of claim 3 wherein said socket means aperture comprises a neck portion of reduced size, said plug means being configured to engage said neck portion and resist plug means removal from said socket.

5. The lead anchoring system of claim 4 wherein said plug means is formed of a resilient material.

6. The lead anchoring system of claim 5 wherein said socket means is formed of a flexible material.

7. The lead anchoring system of claim 3 wherein said socket means is formed of a flexible material.

8. The lead anchoring system of claim 3 wherein said socket means further comprises means for facilitating a temporary closing of said grommet means split.

9. The lead anchoring system of claim 8 wherein said burr hole engaging means comprises circumferential rib means.

10. The lead anchoring system of claim 9 wherein said socket means further comprises flange means.

11. The lead anchoring system of claim 10 wherein said facilitating means comprises means formed within said flange means.

12. The lead anchoring system of claim 2 wherein said burr hole engaging means further comprises circumferential rib means carried by the outer wall of said grommet means.

13. The lead anchoring system of claim 1 wherein said socket means aperture comprises a neck portion of reduced size, said plug means being configured to engage said neck portion and resist plug means removal from said socket.

14. The lead anchoring system of claim 13 wherein said plug means is formed of a resilient material.

15. The lead anchoring system of claim 14 wherein said socket means is formed of a flexible material.

16. The lead anchoring system of claim 1 wherein said burr hole engaging means comprises circumferential rib means.

17. The lead anchoring system of claim 1 wherein said socket means further comprises flange means.

* * * * *